United States Patent [19]

Perdijon

[11] Patent Number: 4,557,145
[45] Date of Patent: Dec. 10, 1985

[54] ULTRASONIC ECHOGRAPHY PROCESS AND DEVICE

[75] Inventor: Jean Perdijon, Saint Ismier, France

[73] Assignee: Compagnie Generale des Matieres Nucleaires, Velizy Villacoublay, France

[21] Appl. No.: 513,329

[22] Filed: Jul. 13, 1983

[30] Foreign Application Priority Data

Jul. 13, 1982 [FR] France ................... 82 12299

[51] Int. Cl.⁴ ............................. G01N 29/04
[52] U.S. Cl. .......................... 73/621; 73/633
[58] Field of Search ................. 73/621, 633, 634; 128/660; 367/104

[56] References Cited

U.S. PATENT DOCUMENTS

| | | | |
|---|---|---|---|
| 3,752,255 | 8/1973 | Hill et al. | 73/633 |
| 3,792,423 | 2/1974 | Becker et al. | 73/620 |
| 4,131,021 | 12/1978 | Mezrich et al. | 73/625 |
| 4,165,647 | 8/1979 | Collins | 73/603 |
| 4,221,132 | 9/1980 | Poole | 73/620 |
| 4,455,872 | 6/1984 | Kossoff et al. | 73/621 |
| 4,457,174 | 7/1984 | Bar-Cohen et al. | 73/633 |

FOREIGN PATENT DOCUMENTS 55-421  1/1980  Japan .................. 73/633

Primary Examiner—Stewart J. Levy
Assistant Examiner—John E. Chapman, Jr.
Attorney, Agent, or Firm—Larson and Taylor

[57] ABSTRACT

For determining zones in a piece (such as cracks) which reflect ultrasounds, an apparatus is provided which comprises a transducer for transmitting a fine ultrasound beam and for receiving ultrasound echo signals. That transducer is moved externally of the piece for scanning it and the coordinates of each zone which returns an echo signal higher than a predetermined threshold in response to an ultrasound pulse are determined. The transducer is moved according to a composite movement which results from the composition of a conical movement about an axis which is orthogonal to a surface of said piece having an apex on the surface and a rectilinear movement parallel to the surface. Consequently, the beam enters the piece after path of constant length out of the piece. Each zone of the piece to be examined receives the beam under a plurality of different azimuth angles and the echo signals returned from a same zone of the piece are combined. An isometric view of the locations of the echoes in the piece is displayed.

6 Claims, 5 Drawing Figures

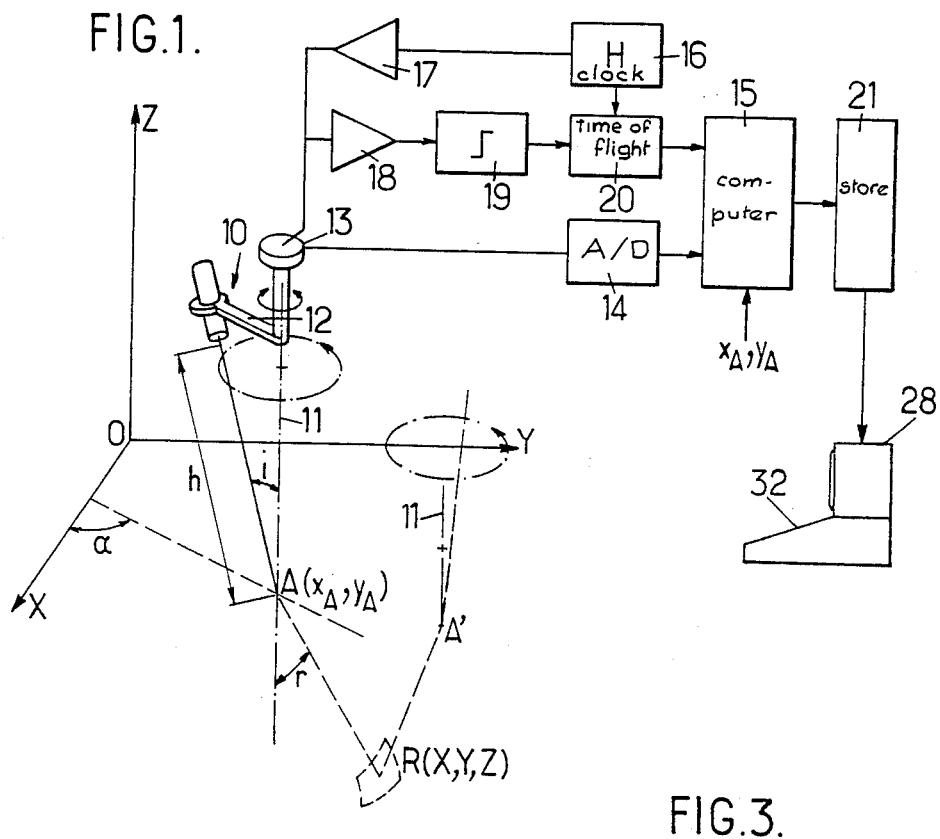
FIG.1.
FIG.3.
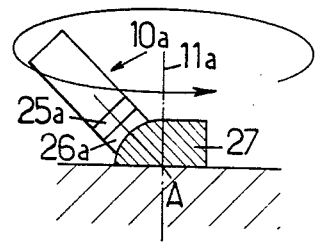
FIG.2.
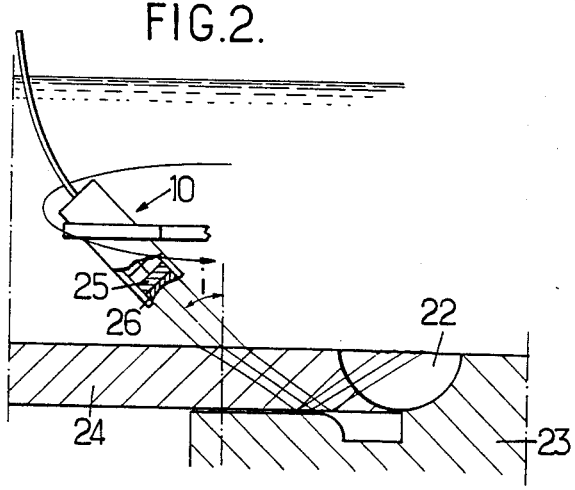

ULTRASONIC ECHOGRAPHY PROCESS AND DEVICE

BACKGROUND AND SUMMARY OF THE INVENTION

The present invention relates to the field of ultrasonic scanning echography and it relates more particularly to an echography process and device for locating the zones of reflection of a fine ultrasonic beam directed into a workpiece through a surface thereof.

The invention finds an important application, although not exclusive, in the non destructive testing of workpieces, and in particular in testing welded or solid pieces in which the cracks form reflectors for the ultrasonic beams directed transversely to the direction of the crack.

Numerous echography processes are already known using scanning of the workpiece to be tested by means of a focussed ultrasonic beam. The principle used is generally the following:

A finely focussed ultrasonic beam is directed into the workpiece. When it meets a reflector, formed by a heterogeneity, an echo is received in return whose amplitude depends on the area of the reflector (if it is less than the section of the beam), its orientation and its reflection coefficient. The echo is collected in general by the transmitting transducer and the reflector may be located by measuring the time of flight. Thus, the contour of a reflector may be determined by selecting the echoes whose attenuation, with respect to the amplitude corresponding to an extended plane reflector having the same orientation, at the same depth, is less than a threshold, 6 dB in general.

As a general rule, the exploration of a workpiece is effected by scanning its surface in two perpendicular directions, with a constant incidence in a plane which, during the exploration, keeps the same orientation with respect to an axis of symmetry of the workpiece. These processes have the serious disadvantage of only allowing reflectors to be detected which are struck by the ultrasonic beam at an incidence not deviating too much from the perpendicular.

Reflectors may then pass unnoticed and this is a particularly serious disadvantage for non destructive testing.

It is an object of the invention to provide an improved echography process. It is a more specific object to provide a process in which the probability of failure to detect zones forming ultrasonic reflectors, such as cracks or flaws in a medium, such as a workpiece, is reduced whatever the azimuth angle of these reflectors (orientation with respect to the perpendicular to the surface of the workpiece).

To this end, there is provided an echography process in which a fine ultrasonic beam is directed into the medium through the surface of said medium and the position of the zone providing an echo for several beam positions is determined and the ultrasonic beam is successively moved along the generatrices of several cones each having a rotation symmetry and having their apex on said surface and their axis perpendicular to said surface, having advantageously the same angle at the apex.

This movement is effected so that the region to be explored receives the beam at several different azimuth angles and in that the echo data corresponding to the same zone and to different azimuth angles is combined to provide a perspective representation of the medium. A isometric projection is provided.

It can be seen that all the signals obtained during scanning of the workpiece and whose data show that they concern the same elementary volume of the piece are superimposed at the same point of the representation. This solution may be used in a simple way, for there already exist on the market numerous computer programmes for providing a perspective representation, often even allowing to rotate it on a display screen such as a CRT.

To obtain high resolution, the ultrasonic beam will generally be formed from a transducer formed from a single wafer of piezoelectric material mounted against a cushioning block so as to obtain short pulses of appropriate shape or associated with an ultrasonic focussing lens.

In general, it will be sufficient to detect, for each orientation, the presence of echoes whose amplitude is greater than the threshold (typically of $-6$ dB with respect to an extended reflector) and to store the coordinates of the zones giving rise to such an echo.

In a variant for providing a more elaborate representation, the amplitude of the high frequency echo signal received is digitized, which corresponds to several gray levels or to arbitrary colors. The medium is considered as consisting of volume elements each centered on a node of a three-dimensional network and all echoes corresponding to a separate one of the volume elements are summed. Such a process leads to improving the signal/noise ratio by averaging the high frequency signal. It is obviously necessary to have available a much higher memory volume, since a memory element must be made to correspond to each volume element of the medium.

The invention also aims at providing an echography apparatus capable of being constructed by the addition of simple and inexpensive components to an existing echography installation already comprising computing means, which apparatus increases the capacity of the device to detect ultrasonic reflectors in the medium whatever the azimuth angle of these reflectors. To this end, an apparatus comprises means for emitting a fine ultrasonic beam and for receiving echoes, a device for moving said means outside the medium so as to provide scanning of this latter, and circuits for computing the coordinates of the zones producing an echo greater than a predetermined threshold device is provided for imparting to said means a scanning movement formed by a rotation about an axis perpendicular to the surface while maintaining them in an orientation such that the beam penetrates into the workpiece along the axis of rotation with a preliminary constant distance of travel, and to repeat this scanning about several axes perpendicular to the surface so that each zone to be examined receives the beam at several different azimuth angles and in comprises means for combining the echoes coming from the same zone so as to provide a perspective representation of their location in the medium.

The computing means will be generally provided for computing the position of the echo sources in a coordinate system related to the workpiece from the travel time of the ultra-sounds, from the position of the axis and from the coordinates of the beam emitting means with respect to the axis.

The invention will be better understood from reading the following description of particular embodiments, given by way of non limiting examples.

SHORT DESCRIPTION OF THE DRAWINGS

FIG. 1 is a diagram showing the magnitudes which come into play during the scanning of a workpiece;

FIG. 2 is a diagram showing one possible application of the invention to the testing of welds in a composite workpiece, shown in section;

FIG. 3 is a simplified diagram showing a probe usable in a variant of the invention, intended for the manual exploration of a workpiece.

DETAILED DESCRIPTION OF A PARTICULAR EMBODIMENT

Although the invention is applicable to the testing of any medium limited by a simple geometric surface, it will be assumed for the sake of simplicity that the workpiece has a flat accessible face through which the exploration will be made. This is frequently the case and the reflectors to be detected have practically all the same orientation in a plane perpendicular to the surface of the workpiece, i.e. the same slope, whereas their azimuth angle (orientation in a plane parallel to the plane of the workpiece, is very variable.

In FIG. 1, a reference triad OXYZ has been shown, the plane OXY merging with the surface of the workpiece. The exploration of this latter is effected by means of an ultrasonic emitting and receiving transducer 10 whose distance h to the input point into the piece is maintained constant. For that, the transducer is moved along a circle, with a slope such that the beam penetrates into the workpiece at an incidence point A corresponding to the intersection of the axis of rotation with the surface of the workpiece. Thus, the preliminary distance covered by the ultrasonic beam, between the transducer 10 and the workpiece, is constant. Moreover, the shape of the beam in the workpiece is not modified.

Generally a focussing transducer 10 will be chosen, supplying a narrow approximately cylindrical beam. Numerous transducers of this type are already known. In general the transducer 10 and the workpiece are immersed in a liquid, such as water, contained in a tank, not shown. The transducer 10 is carried by a bracket 12 giving to the transducer a predetermined distance h with respect to the workpiece and a given slope. This bracket forms part of an assembly rotatable about axis 11, comprising means 13 for measuring the angular position of the bracket, supplying the angle $\alpha$ of the translator about axis 11.

Figure 1A:
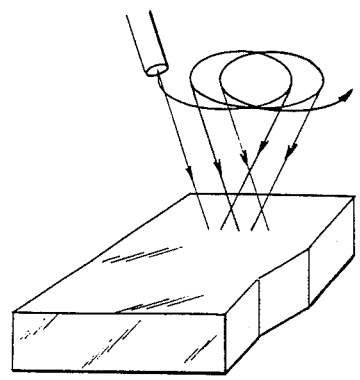
FIG. 1A is a diagram showing one type of possible scanning for implementing the invention.

Such a device allows several successive angular scans to be made about axes perpendicular to the workpiece, for example axes 11 and 11' in FIG. 1. To avoid the need to provide rotary seals for the electrical supply of the transducer, the mobile assembly may be provided for oscillation between two endmost positions defined by stops rather than rotation always in the same direction. Rotating mirrors may also be used, although they lengthen the preliminary travel distance before the beam enters the part. A translational movement in for example direction Y and a conical movement (FIG. 1A) may also be combined. In all cases, the translational movement between two 360° rotations of translator 10 and the angle of incidence i are chosen while taking into account the transverse dimension of the beam so that each volume element of the part to be examined of the workpiece receives the beam at least twice at different azimuth angles.

Determination of the coordinates X,Y,Z of the first reflector met by an ultrasonic beam during a given shot, corresponding to given values of h, i and $\alpha$ may always be achieved by a simple computation, more especially when the input surface of the ultrasonic beam is plane. In fact, the preliminary distance travelled by the ultrasonic beam in the liquid remains constant and equal to h. With the notations given in FIG. 1, it can be seen that the appearance of an echo S of a level greater than the threshold is related to the presence of a reflector R in the workpiece by the relationships:

$$X = x + (h \sin i + c_1 t \sin r) \cos \alpha \tag{1}$$

$$Y = y + (h \sin i + c_1 t \sin r) \sin \alpha \tag{2}$$

$$Z = -c_1 t \cos r \tag{3}$$

Since the computer may receive the digitized coordinates $x_A$ and $y_A$ of point A, given by encoders located on a table carrying the bracket 12, it is not necessary to go back to the coordinates Y, Y of the center of the emitter and the coordinates of the reflector are obtained by the following system of equations (1'), (2') and (3') which contains neither h, nor the angle of incidence i:

$$X = x_A + c_1 t \sin r \cos \alpha \tag{1'}$$

$$Y = y_A + c_1 t \sin r \sin \alpha \tag{2'}$$

$$Z = -c_1 t \cos r \tag{3'}$$

In this formula, t designates the outgoing (or return) time in the workpiece, r the angle of refraction (deduced from i by Descartes law), $\alpha$ the azimuth angle of the translator 10; h, r and the velocity of propagation $c_1$ are known and constant.

In practice the invention will be generally used in an existing installation, already provided with a tank with XY scanning, such for example as the tank manufactured and sold by the Compagnie Générale de Radiologie under the reference CE2. The measuring system of this tank may provide the coordinates $x_A$ and $y_A$ of point A along OX and OY. An angle of rotation measuring sensor with digital output or provided with an analog-digital converter 14, supplies the value of $\alpha$ to a computer 15 which also receives the digitized coordinates of A.

The detection of the echoes with an amplitude greater than the threshold may be effected conventionally, by using for example a circuit of the kind shown in FIG. 1, where it is assumed that the speed of rotation of the transducer 10 is sufficiently low for it to be possible to use the same transducer for emitting and receiving. The circuit comprises a clock 16 delivering, at regular intervals, pulses which are amplified at 17 and applied to the transducer. The return signals, amplified at 18, are applied to a threshold detector 19. The travel time between emission and reception of an echo greater than the threshold is measured by a circuit 20 which also drives the computer 15. The coordinates XYZ of each echo selected are stored by the computer in a memory 21.

It should be noted in passing that the relationships between coordinates are more complex when the workpiece does not have a plane surface, but in general the above relationships 1, 2 and 3 will be sufficient since they provide a planar representation of a curved workpiece.

The table for movement along OX and OY allows conical explorations of the workpiece to be effected about successive axes 11. Two axes 11 and 11' have been shown in FIG. 1 and it can be seen that the reflector R, formed for example by a crack or a split, will appear much better during scanning about axis 11 than during scanning about axis 11', since the beam directed into the workpiece along A'-R is in this latter case almost parallel to the direction of the reflector.

A small-size computer will in general be sufficient, for example of the type HP 85 (HEWLETT-PACKARD), possibly completed by additional memories. At the end of scanning of the workpiece about a number of successive axes 11 which will depend on the dimensions of the piece, computer 15 restitutes the coordinates of each zone corresponding to a significant echo signal. The restitution may in particular be in the form of a perspective representation of the workpiece on the screen of the monitor associated with the computer. Possibly this image may be stored then compared, added to or subtracted from an image obtained under different conditions, for example with a different angle i.

Figure 4:
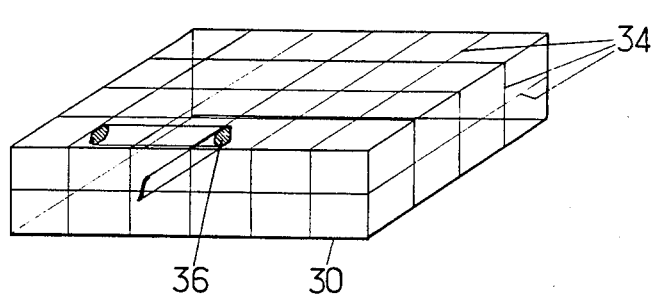
FIG. 4 shows schematically the perspective representation of a reflector on a display means.

FIG. 4 shows display on a monitor 28 forming the output unit of a computer 21 in which a program has been stored for isometric representation. Numerous programs for providing a isometric display are available from the hardware manufacturers and they need not be described here. The shape of workpiece 30, which will be assumed to be parallelpipedic, is defined by introducing, by means of keyboard 32, the coordinates of its corners along OX, OY and OZ; from this data, the computer elaborates a regular grid 34 showing the shape of the workpiece.

For each pulse, the computer computes the coordinates X, Y and Z of the reflectors and it carries out transcoding consisting in an approximating operation assigning to the reflector the coordinates $X_1$, $Y_1$, $Z_1$ of the nearest point of a given grid, denser than grid 34, displayed and chosen as a function of the width of the beam; each node of the grid defines thus a volume element. The successive echoes obtained for different azimuth angles are summed and provide an overall isometric projection, such as the one shown at 36 in FIG. 4. The program may be selected to further provide a representation of the location of the echo as projected on two mutually perpendicular surfaces.

It can be seen that the invention may be implemented under conditions adapted to each particular case and that numerous parameters may be selected for better complying with the nature of the workpiece and with the type of anomaly to be detected.

By way of example, one possible application of the invention is shown in FIG. 2 for detecting the possible cracks in a hexagonal welding bead 22 between a plug 23 and a tube with hexagonal section 24, both made from steel. The transducer 10 is formed by a barium titanate wafer 25 at least 10 mm in diameter, placed between a cushioning block and a focussing lens 26. In general, a wafer will be used whose resonance frequency is between 2 and 10 MHz. The angle of incidence i will be selected depending on the nature of the waves used (longitudinal waves if it is desired to promote travel through the metal, transverse waves if it is desired to strengthen the echoes). Tests have essentially been carried out with a transducer having a focal length of about of 50 mm, working with transverse waves at 5 MHz, the wafer 25 having a diameter of 10 mm. The preliminary path h in the water of the tank was 24 mm. The angle of incidence i was 25° and led to an average refraction angle of 70° and to a reflection angle from the internal surface of the same order. The circle of least diffusion of the beam (corresponding to the focal length from the transducer) was thus situated approximately at the joint plane within the weld. The workpiece is immersed in a tank of the type commercialized by CGR under the name CF2. The bead is explored face by face, in several passes made parallel to the bead, with a pitch of about 0.5 mm. The appearance during this exploration of a signal greater than the fixed threshold, triggers off the measurement of its time of flight with respect to the input echo, that of $\alpha$ (given digitally by an optical encoder) and the digital conversion of the measurements $x_A$ and $y_A$, supplied analogically by the tank. These measurements are stored in a buffer memory then transferred to the computer at each line end. The computer, of type HP 85, gives at the end of scanning a perspective view on its screen and allows cross section or maps to be output on a plotting table.

Numerous modifications are available. In particular, as was mentioned above, the whole of the high frequency signal received after the input echo may be processed and its level stored in quantified form, which however requires the use of a more powerful computer. On the contrary manual exploration may be carried out, advantageously in real time so as to identify rapidly the zones to be studied in greater detail. In this case, it is desirable to operate by contact, with a shoe transducer 10a which may be of the kind shown in FIG. 3. The transducer 10A again has a piezoelectric wafer 25a, the focussing is provided by a lens 26a in contact with a metal connecting shoe capable of rotating about the axis 11a, or by curvature of the wafer, which avoids the interpositioning of two different media, one for the lens and the other for the shoe. A thin coupling liquid film is interposed between the shoe 27 and the surface of the workpiece. In this case, it will be generally preferable to set the position of transducer 10a in polar coordinates with respect to the system of axes related to the workpiece, as well as its orientation with respect to the vector radius OA.

I claim:

1. A process for echographic detection of ultrasound reflecting zones in a piece, including the steps of: directing successive fine ultrasonic beam pulses from a transducer into said piece across a surface of said piece along a plurality of different genatrix lines of a plurality of successive cones each having a rotational symmetry about an axis orthogonal to said surface, and whose apexes are on said surface and with a constant path length from said transducer to said surface, while providing translational movement of said transducer such that each zone in a region to be scanned in said piece receives at least two pulses corresponding to different azimuth angles; determining the location of each of the zones which provide an echo signal; combining the echo signals corresponding to each of said zones which provide an echo signal and corresponding to different azimuth angles; and displaying the combination of echo signals on an isometric representation of each piece.

2. A process according to claim 1, wherein the echo signal received from each of a plurality of elementary volumes of the piece which are each centered on a node of a three dimensional array in said piece is digitized and the digitized signals corresponding to each of the elementary volumes are summed.

3. A process according to claim 1, further comprising the steps of measuring the location of said transducer and the azimuth angle of the ultrasonic beam delivered by said transducer upon occurence of each of said ultrasonic beam pulses and computing the coordinates of each zone which provides an echo signal in a triad bound to said piece from said location and said azimuth angle and from the time of flight of the pulse.

4. A process according to claim 1, wherein said echo signals are combined by comparing the echo signals to a predetermined threshold and retaining only those of said echo signals which are greater than said threshold and providing a representation of each zone by summing all of said retained echo signals originating from said zone.

5. Apparatus for determining all zones in a piece which reflect ultrasounds, comprising: first means for transmitting a fine ultrasound beam and for receiving ultrasound echo signals; second means for moving said first means externally of said piece for scanning said piece; and circuit means for determining the coordinates of all zones which return an echo signal higher than a predetermined threshold; said second means being arranged for moving said first means according to a composite movement which results from the composition of a rotation about an axis which is orthogonal to a surface of said piece while maintaining said beam in an angular position oblique with respect to said surface and such that the beam enters the piece with a constant path length and of a rectilinear movement parallel to said surface, whereby each zone of said piece which is to be examined receives the beam under a plurality of different azimuth angles, means being provided for combining the echo signals returned from the same zone of said piece and for providing an isometric display of the zones producing each echo in the piece.

6. Apparatus for detecting ultrasound reflecting cracks and flaws in a piece, comprising:
transducer means for transmitting a fine ultrasound beam and for receiving ultrasound echo signals;
first means arranged to receive said transducer means and to rotate said transducer means along a circular path while maintaining said transducer means in such a direction that the ultrasound beam delivered by said transducer means is moved along a cone having a rotational symmetry about an axis which is orthogonal to said surface, whereby the beam has a path of constant length to said piece before it enters the piece,
and second means arranged for moving said first means and said transducer means as a whole along a rectilinear path parallel to said surface at the same time the transducer means is being rotated by the first means so as to provide a composite movement of said transducer means,
means for measuring the extent of rotational movement and the extent of rectilinear movement of said transducer means,
and means for combining echo signals returned from the same zone of said piece for different positions of said transducer means and for providing an isometric display of the location of the ultrasound reflecting cracks and flaws in said piece.

* * * * *